United States Patent [19]

Zondler

[11] 4,151,229
[45] Apr. 24, 1979

[54] PROCESS FOR THE MANUFACTURE OF AMINOALKYL-PHOSPONIC ACID ESTERS

[75] Inventor: Helmut Zondler, Allschwil, Switzerland

[73] Assignee: Ciba-Geigy Corporation, Ardsley, N.Y.

[21] Appl. No.: 574,196

[22] Filed: May 2, 1975

Related U.S. Application Data

[63] Continuation of Ser. No. 415,601, Nov. 14, 1973, abandoned.

[51] Int. Cl.$^2$ ............................................. C07F 9/38
[52] U.S. Cl. ................................................. 260/968
[58] Field of Search ......................................... 260/968

[56] References Cited

U.S. PATENT DOCUMENTS

| 3,812,221 | 3/1974 | Braden et al. | 260/968 |
| 3,813,456 | 5/1974 | Kerst | 260/968 |

Primary Examiner—Anton H. Sutto
Attorney, Agent, or Firm—Vincent J. Cavalieri

[57] ABSTRACT

The invention relates to a process for the manufacture of aminoalkyl-phosphonic acid esters by catalytic hydrogenation of cyanoalkylphosphonic acid esters. After having separated the catalyst and solvents, in general the crude product is distilled.

The esters which can be obtained by the process of this invention are of importance as intermediate products, because all reactions of amines can be carried out with these products. They can also be used as additives for amine curing agents for epoxide resins in order to achieve flame-retarding properties.

8 Claims, No Drawings

PROCESS FOR THE MANUFACTURE OF AMINOALKYL-PHOSPONIC ACID ESTERS

This is a continuation of application Ser. No. 415,601 filed on Nov. 14, 1973, now abandoned.

ω-Aminoalkyl-phosphonic acid compounds are known to be of particular importance as intermediate products which lend themselves very readily to the manufacture of flameretarding and surface-active substances. In this context attention should be drawn, for example, to German Offenlegungsschrift No. 2,032,712, which in addition to the detailed description of the process claimed therein on page 1 also contains notes on known processes for the manufacture of aminoalkyl-phosphonic acid derivatives. At the same time, the disadvantages of these known processes are also singled out.

The said Offenlegungsschrift also shows that vain attempts have been made to hydrogenate ω-cyanoalkyl-phosphonic acid dialkyl esters in order thus to obtain the particularly valuable ω-aminoalkyl-phosphonic acid esters (see page 2, 1st paragraph). The products obtained were not the desired ω-aminoalkyl-phosphonic acid esters but non-volatile condensation products which were not investigated in more detail. Such unusable compounds were also to be expected as, because of the amino groups produced and the ester groups present, it had to be expected that intermolecular and intramolecular amide formation would occur (analogously to peptide formation in the case of esters of aminoacids).

Admittedly, several other processes for the manufacture of aminoalkyl-phosphonic acid dialkyl esters are known. These, however, are technically very involved, and entail high costs, because of the expensive starting products, the multi-stage procedure which is required, and the low yields. Such uneconomical processes are described, for example, in the following publications:

1. T. A. Mastryukova et al, Chem. Abstr. 75, 76947 h (1971)
2. A. N. Pudovik et al, Chem. Abstr. 48, 2572 (1954)
3. T. Mukaiyama, Bull. Chem. Soc. Jap. 39, 1297–1301 (1966)

These detailed communications on the known procedures further indicate the industrial importance of aminoalkyl-phosphonic acid esters and the need for more advantageous manufacturing processes.

The task of the invention, namely to discover a better process for the manufacture of aminoalkyl-phosphonic acid esters, was solved by hydrogenating cyanoalkyl-phosphonic acid esters under mild conditions and working up the resulting end products under mild conditions. However, in this hydrogenation reaction it is important to start from cyanoalkyl-phosphonic acid esters wherein the ester groups are derived from ethyl alcohol, from longer-chain, branched or cyclic alcohols or from dialcohols. Cyanoalkyl-phosphonic acid dimethyl esters, on the other hand, are unsuitable for the process according to the invention.

The subject of the invention is a process for the manufacture of aminoalkyl-phosphonic acid esters of the general formula I

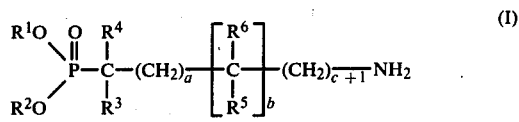

in which $R^1$ and $R^2$ are identical or different and denote an unbranched or branched alkyl radical with 2 to 10 carbon atoms, a cycloaliphatic radical or, together, an alkyl-substituted or unsubstituted propylene radical, a, b and c are identical or different and a and c denote a number from 0 to 5 and b denotes 0 or 1, $R^3$ represents hydrogen, an alkyl radical with 1 to 10 carbon atoms, phenyl or furyl and $R^4$, $R^5$ and $R^6$ are identical or different and denote hydrogen or the methyl group, which is characterised in that a cyanoalkyl phosphonic acid ester of the general formula II

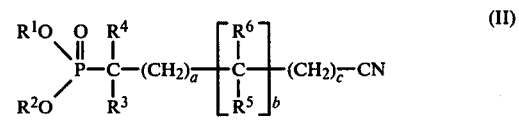

is hydrogenated catalytically at temperatures of about 20° to 150° C. and the resulting product is freed in a known manner from the catalyst and solvents and is optionally distilled, preferably in a high vaccum.

In view of the previously vain attempts by those skilled in the art to manufacture the corresponding ω-aminoalkyl compounds by hydrogenation of ω-cyanoalkyl-phosphonic acid dialkyl esters, and also in view of the chemical structure of the cyanoalkyl compounds which are used as the starting materials according to the invention, the elegant solution of the task of the present invention was surprising.

The temperature suitable for the hydrogenation according to the invention however in each case depends on the hydrogenation catalyst used. Where Raney nickel or Raney cobalt is used, the procedure for optimum yield is to use temperatures of about 60° to 120° C. If known noble metal catalysts, such as platinum, palladium, rhodium or ruthenium are used, it is also possible to work at lower temperatures such as, say, at room temperature.

The hydrogenation can be carried out according to the methods which are customary in the laboratory and in industry, either without the use of pressure, for example in a duck-shaped shaking vessel, or under pressure in an autoclave. The presence of gaseous ammonia has a favourable effect on the nitryl hydrogenation according to the invention.

The solvents which can be used for the hydrogenation are the organic solvents which are usually employed together with the abovementioned types of catalyst, especially alcohols, hydrocarbons or ethers, such as methanol, ethanol and dioxane, or aromatic compounds, such as toluene or benzene.

The catalytic reduction is as a rule carried out by mixing the solution of the particular cyanoalkylphosphonic acid ester with the catalyst and passing hydrogen gas into the reaction mixture. The hydrogenation is continued until no further hydrogen is absorbed. After completion of the hydrogenation, the catalyst is removed, for example by filtration, and the solvent is distilled off in vacuo at moderate temperatures.

In some cases it suffices if the end product is merely freed of catalyst and solvent in the manner described. The crude aminoalkylphosphonic acid ester thus obtained can then be used further direct, that is to say undistilled.

Frequently, however, the degree of purity of the products obtained according to the process of the invention has to meet higher standards. According to the invention, the product is, in such cases, distilled at pressures which are as low as possible, especially in a high vacuum. The requisite conditions for the distillation can, admittedly, vary from product to product. In the case of substances of low molecular weight, a vacuum of a few mm Hg frequently suffices and only temperatures of up to about 100° C. are required. In most cases, however, a high vacuum will be required for the distillation. The end products should if possible be distilled at pressures which result in boiling points below about 150° to 170° C.

Preferably, the distillation is carried out under so-called "gentle conditions", that is to say at temperatures which are as low as possible. A gentle distillation is in most cases ensured through the use of a thin layer evaporator.

If, because of the molecular structure or of the molecular weight, a distillation under gentle conditions should not be possible, the resulting crude amine could either be used undistilled or could be purified in some other way. As regards the latter, purification by elution or extraction of the liquid product with suitable organic solvents would be conceivable, for example.

As a further method of purification of the crude amines, conversion of the latter into salts, recrystallisation of the salts and re-liberation of the amines by addition of base should be mentioned.

The starting products employed preferentially for the process according to the invention are those in which the individual radicals of the formula II have the following meaning: $R^1$ and $R^2$ each denote a branched alkyl group with the branching in the α- or β-position to the oxygen atom and with a total of 3 to 8 C atoms; $R^3$ denotes hydrogen, methyl, phenyl or furyl and $R^6$ denotes hydrogen. Further preferred starting products employed are those in which an unbranched or branched alkylene radical with a total of 1 to 3 C atoms is present between the P atom and the nitrile group. $R^1$ is in most cases identical to $R^2$.

The following cyanoalkyl-phosphonic acid esters are examples of starting substances of the formula II which can be used for the process according to the invention:
Cyanomethyl-phosphonic acid diethyl ester
β-cyanoethyl-phosphonic acid diethyl ester
2-cyanopropyl-phosphonic acid diethyl ester β-cyanoethyl-phosphonic acid diisobutyl ester
2-(β-cyanoethyl)-5,5-dimethyl-2-oxo-1,3,2-dioxaphosphorinane
3-cyanopropyl-phosphonic acid diethyl ester
ω-cyanodecyl-phosphonic acid diethyl ester
(β-cyano-α-phenyl)-ethyl-phosphonic acid diisopropyl ester
(β-cyano-α-methyl)-ethyl-phosphonic acid diethyl ester and
(β-cyano-α-furyl)-ethyl-phosphonic acid diisopropyl ester.

The cycloalkyl-phosphonic acid esters of the formula II employed as starting products can be manufactured in various ways.

Thus, the base-catalysed addition of olefines, in which the double bond is activated by a nitrile group, to esters of phosphorous acid is known. Examples of nitriles which can be employed are acrylonitrile, methacrylonitrile or crotonic acid nitrile. The addition reaction takes place, for example, according to the following equation:

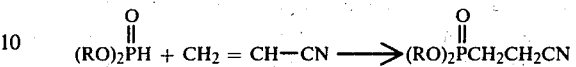

This method of manufacture is described in the following publications:

A. N. Pudovik and G. A. Golitsyna Zh. Obshch. Khim. 34 (3), 876–81 (1964); compare Chem. Abstr. 60, 15904 (1964).

A. N. Pudovik and B. A. Arbuzov, Akad. Nauk. SSSR 73, 327–30 (1950); compare Chem. Abstr. 45, 2853 b (1951).

A. N. Pudovik and B. A. Arbuzov, Zhur. Obshch. Khim. 21, 1837–41 (1951); compare Chem. Abstr. 46, 6082 e (1952).

B. Bochwic and J. Michalski; Roczniki Chem. 25, 338–49 (1951); compare Chem. Abstr. 48, 12013 (1954).

U.S. Pat. No. 2,899,455.

A further method of manufacture of the starting products according to the formula II is the addition, by radical mechanisms, of esters of phosphorous acid to compounds with isolated olefinic double bonds, which are described in the reference book "Methoden der organischen Chemie" ("Methods of Organic Chemistry"), volume XII/1, by Houben-Weyl, on page 463. Such reactions take place according to the following equation:

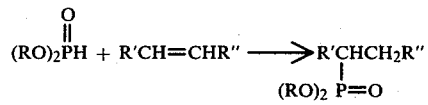

If the olefine contains a nitrile group, cyanoalkylphosphonic acid esters are again obtained. As such unsaturated nitriles it is possible to use, for example, straight-chain compounds such as allyl cyanide or undec-(1)-ene-(11)-nitrile $(CH_2=CH(CH_2)_8CN)$, or branched compounds such as

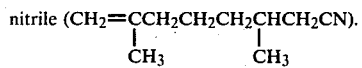

A third possible method of manufacture of the cyanoalkyl-phosphonic acid esters according to the formula II is the reaction of nitriles containing halogen with trialkyl-phosphites in a so-called Arbuzov reaction. In this, the cyanoalkyl-phosphonic acid esters are obtained, with elimination of alkyl halides. The reaction takes place according to the following equation:

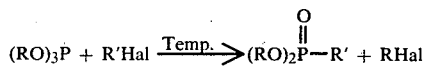

(Herein, R' denotes a radical containing a nitrile group).

Examples of such nitriles containing halogen are chloroacetonitrile, 3-chloropropionitrile or 5-chloro-n-valeronitrile.

The Arbuzov reaction is described in more detail in, for example, the following publications:

D.T.-Patent 1,108,208,

M. Kirilov and J. Petrova, Comp. Rend. Acad. Bugare Sci. 17 (1), 45-8 (1964), compare Chem. Abstr. 61, 8335 (1964) and P. Teissier, M. Plattier and B. Corbier; Recherches (Paris) No. 14, 44-56 (1964), compare Chem. Abstr. 63, 14913 (1965).

A fourth process to be mentioned for the manufacture of nitrile compounds according to the formula II is the alkylation of cyanomethyl-phosphonic acid esters with alkyl halides, which is also described in DT-Patent 1,108,208. Cyanomethyl-phosphonic acid esters which are monosubstituted in the α-position are obtained according to the following equation:

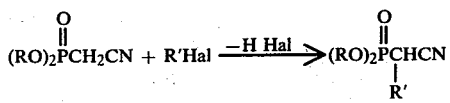

The aminoalkyl-phosphonic acid esters which can be manufactured according to the process of the invention, being amines, are of particular importance as intermediate products. This is because in principle all reactions of amines can be carried out with these products. One possible way of using them directly is to add these products to amine curing agents for epoxide resins to achieve flameretarding properties.

The substantial simplification of the manufacture of aminoalkyl-phosphonic acid esters by the process according to the invention as compared to the processes according to the state of the art is illustrated in the examples which follow.

EXAMPLE 1

β-Aminoethyl-phosphonic acid diethyl ester

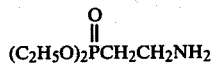

136 g of cyanomethyl-phosphonic acid diethyl ester in a mixture of 450 ml of ethanol and 150 g of gaseous ammonia are hydrogenated in the presence of 13 g of Raney nickel at 70° C. in an autoclave under a hydrogen pressure of 80 atmospheres gauge for 8 hours. After filtering off the catalyst, the filtrate is concentrated on a rotary evaporator under a pressure of 15 mm Hg and at a bath temperature of at most 60° C., and the residue is freed of low-boiling constituents at 75° bath temperature under a pressure of 0.2 mm Hg in a distillation apparatus, using a boiling capillary. 138 g of the crude amine, which according to titration with acid contains 4.73 amine equivalents per kg (theoretical, 5.52 equivalents/kg) are obtained. For further purification, 132.4 g of crude amine were distilled in a high vacuum without a column, giving 105.0 g (76.0% of theory) of boiling point 59° C./0.014 mm Hg to 65° C./0.027 mm Hg, of more than 95% purity according to gas chromatography. Titration gave a degree of purity of 98.8%.

1.57 g of picrate of melting point 137°-139° C. can be obtained from 1.15 g of picric acid and 900 mg of pure amine, from a mixture of 6 ml of ethanol and 6 ml of benzene.

Analysis of the picrate $C_6H_{16}NO_3P \times C_6H_3N_3O_7$ (M=410.28).

Calculated: C 35.1; H 4.7; N 13.7. Found: C 35.5; H 4.9; N 13.7.

EXAMPLE 2

Y-Aminopropyl-phosphonic acid diethyl ester

250 g of β-cyanoethyl-phosphonic acid diethyl ester in a mixture of 750 ml of ethanol and 250 g of gaseous ammonia are hydrogenated over the course of 3 hours in the presence of 25 g of Raney nickel in an autoclave at 65°-70° C. and under a pressure of 100 atmospheres gauge. After working up as in Example 1, 254.9 g of crude amine are obtained, of which the volatile constituents consist to the extent of more than 90% of the above compound, according to the gas chromatogram. For further purification, the material is distilled in a high vacuum without a column, giving 211.2 g (82.8% of theory) of boiling point 68° C./0.012 mm Hg to 75° C./0.015 mm Hg. The liquid amine is more than 95% pure according to gas chromatography.

Analysis $C_7H_{18}NO_3P$ (M=195.20). Calculated: C 43.07; H 9.30; N 7.18. Found: C 42.95; H.9.05; N 6.88.

The mass spectrum gives a molecular peak at m/e 195. Using high resolution, Y-(ethylamino)-propyl-phosphonic acid diethyl ester, which is present in amounts of less than 5% and has a molecular peak at m/e 223, is detectable.

Y-Aminopropyl-phosphonic acid diethyl ester in ethanol forms a picrate of melting point 152°-154° C.

Analysis of the picrate $C_7H_{18}NO_3P \times C_6H_3N_3O_7$ (M=424.31). Calculated: C 36.80; H 4.99; N 13.20. Found: C 36.78; H 5.11; N 12.99.

If Y-aminopropyl-phosphonic acid diethyl ester is left to stand at room temperature for some weeks, crystals generally separate out, which after repeated recrystallisation melt at 240°-244° C. with decomposition. As was shown by means of the NMR spectrum, these crystals are the cyclic phosphonamide of the structure

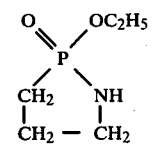

EXAMPLE 3

(Y-Amino-β-methyl)-propyl-phosphonic acid diethyl ester

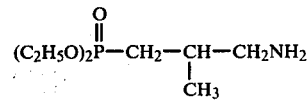

102.5 g of 2-cyanopropyl-phosphonic acid diethyl ester in a mixture of 300 ml of ethanol and 100 g of gaseous ammonia are hydrogenated in the presence of 10 g of Raney nickel for 12 hours in an autoclave at 80° C. and a hydrogen pressure of 100 atmospheres gauge. After working up as in Example 1, 101.5 g of crude amine are obtained; according to titration with acid, this crude amine contains 4.45 amine equivalents per kg (theoretical 4.78 equivalents per kg) and according to the gas chromatogram its volatile constituents consist to the extent of approx. 95% of the above amine. For further purification, the material is distilled in a high vacuum without a column, giving 89.0 g (81.3% of theory) of the liquid amine of boiling point 81°–85° C./0.019 mm Hg in more than 95% purity.

Analysis $C_8H_{20}NO_3P$; (M=209.23). Calculated: C 45.93; H 9.64; N 6.69. Found: C 46.27; H 9.88; N 6.60.

1.15 g of picric acid and 1.04 g of amine in 10 ml of ethanol give 1.65 g of picrate of melting point 140°–142° C.

Analysis of the picrate $C_8H_{20}NO_3P \times C_6H_3N_3O_7$ (M=438.33). Calculated: C 38.36; H 5.29; N 12.78. Found: C 38.51; H 5.56; N 12.81.

EXAMPLE 4

Y-Aminopropyl-phosphonic acid diisobutyl ester

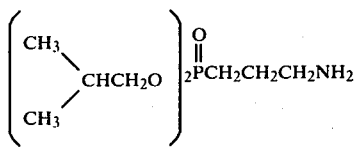

100 g of β-cyanoethyl-phosphonic acid diisobutyl ester in 500 ml of ethanol and 150 g of gaseous ammonia are hydrogenated for 7 hours in the presence of 10 g of Raney nickel at 80° C. and a hydrogen pressure of 100 atmospheres gauge. After working up as in Example 1, 99.9 g of crude amine are obtained; according to titration with acid, this crude amine contains 3.84 amine equivalents per kg (theoretical, 3.98 equivalents per kg), and according to the gas chromatogram its volatile constituents consist to the extent of more than 90% of the above amine. It is purified by distillation in a high vacuum without a column, whereby 89.3 g (88.0% of theory) of the liquid amine of boiling point 101°–110° C./0.020 mm Hg are obtained in approx. 95% purity.

Analysis $C_{11}H_{26}NO_3P$; (M=251.31). Calculated: C 52.57; H 10.43; N 5.57. Found: C 52.22; H 10.55; N 5.96.

EXAMPLE 5

2-(Y-Aminopropyl)-5,5-dimethyl-2-oxo-1,3,2-dioxaphosphorinane

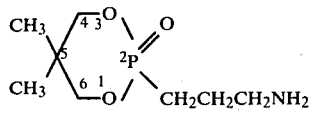

100 g of 2-(β-cyanoethyl)-5,5-dimethyl-2-oxo-1,3,2-dioxa phosphorinane in 800 ml of ethanol and 200 g of gaseous ammonia are hydrogenated for 3 hours in the presence of 10 g of of Raney nickel in an autoclave at 75° C. and a hydrogen pressure of 60 atmospheres gauge. After working up as in Example 1, 105 g of crude amine are obtained; this solidifies at room temperature and according to titration with acid contains 4.32 amine equivalents per kg (theoretical, 4.82 amine equivalents per kg). It is purified by distillation in a high vacuum without a column, whereby 67.7 g (66.4% of theory) of boiling point 135°–139° C./0.015 mm Hg are obtained in more than 95% purity. The amine is solid at room temperature.

Analysis $C_8H_{18}NO_3P$; (M=207.21). Calculated: C 46.37; H 8.76; N 6.76. Found: C 46.20; H 9.34; N 6.20.

With picric acid in ethanol, the amine forms a picrate of melting point 239°–240° C. (decomposition).

Analysis of the picrate $C_8H_{18}NO_3P \times C_6H_3N_3O_7$ (M=436.32). Calculated: C 38.54; H 4.85; N 12.84. Found: C 38.47; H 4.89; N 13.08.

EXAMPLE 6

(Y-Amino-α-methyl)-propyl-phosphonic acid diethyl ester.

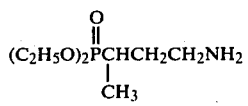

90 g of (β-cyano-α-methyl)-ethyl-phosphonic acid diethyl ester in a mixture of 400 ml of ethanol and 100 g of ammonia are hydrogenated for 5 hours in the presence of 10 g of Raney nickel in an autoclave at 70°–75° C. and a pressure of 80 atmospheres gauge. After working up as in Example 1, 90.9 g of crude amine are obtained containing, as ascertained by titration with acid, 4.47 amine equivalents per kg (theoretical 4.78 equivalents per kg). The material is further purified by distillation in a high vacuum without a column, whereby 77.6 g (84.5% of theory) of amine of boiling point 65° C./0.005 mm Hg are obtained.

Analysis $C_8H_{20}NO_3P$ (M=209.23) Calculated: C 45.93; H 9.64; N 6.69. Found: C 45.84; H 9.79; N 6.71.

In ethanol, the amine forms a picrate of melting point 165°–167° C.

Analysis $C_8H_{20}NO_3P \times C_6H_3O_7N_3$ (M=438.33). Calculated: C 38.36; H 5.29; N 12.78. Found: C 38.54; H 5.39; N 13.06.

EXAMPLE 7

ω-Aminobutyl-phosphonic acid diethyl ester.

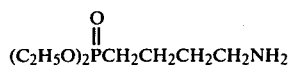

37.6 g of Y-cyanopropyl-phosphonic acid diethyl ester in a mixture of 400 ml of ethanol and 100 g of ammonia are hydrogenated over the course of 5 hours in the presence of 5 g of Raney nickel in an autoclave at 80° C. and a hydrogen pressure of 80 atmospheres gauge. After working up as in Example 1, 34.7 g of crude amine are obtained, containing (as shown by titration with acid) 4.26 amine equivalents per kg (theoretical, 4.78 equivalents per kg). For further purification, the material is distilled in a high vacuum, whereby 28.1 g of amine of boiling point 77° C./0.002 mm Hg are obtained.

Analysis $C_8H_{20}NO_3P$ (M=209.23). Calculated: C 45.93; H 9.64; N 6.69. Found: C 46.14; H 9.65; N 6.81.

In a mixture of ethanol and benzene, the amine forms a picrate of melting point 155°–156° C.

Analysis $C_8H_{20}NO_3P \times C_6H_3N_3O_7$ (M=438.33). Calculated: C 38.36; H 5.29; N 12.78; P 7.07. Found: C 38.75; H 5.31; N 12.96; P 7.09.

EXAMPLE 8

ω-Aminopentyl-phosphonic acid diethyl ester.

57.5 g of δ-cyanobutyl-phosphonic acid diethyl ester in a mixture of 400 ml of ethanol and 100 g of ammonia are hydrogenated over the course of 6 hours in the presence of 10 g of Raney nickel in an autoclave at 80° C. and a pressure of 70 atmospheres gauge. Working up as in Example 1 gives 56.6 g of crude amine which (as shown by titration with acid contains 4.23 amine equivalents per kg (theoretical, 4.48 equivalents per kg). On distillation in a high vacuum, 47.3 g of amine of boiling point 90° C./0.003 mm Hg are obtained.

Analysis $C_9H_{22}NO_3P$ (M=223.25). Calculated: C 48.42; H 9.93; N 6.27; P 13.87. Found: C 48.35; H 9.99; N 6.19; P 13.70.

EXAMPLE 9:

Y-Aminopropyl-phosphonic acid diisopropyl ester

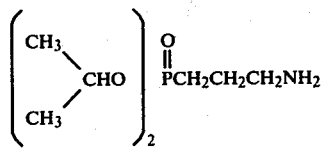

500 g of β-cyanoethyl-phosphonic acid diisopropyl ester in a mixture of 1,000 ml of isopropanol and 350 g of gaseous ammonia are hydrogenated over the course of 2 hours in the presence of 40 g of Raney nickel in an autoclave at 100° C. and a pressure of 100 atmospheres gauge. After filtering off the catalyst and concentrating the filtrate on a rotary evaporator, the crude amine is distilled in a high vacuum without a column. 493.6 g (97.0%) of amine of boiling point 74° C./0.018 mm Hg to 86° C./0.025 mm Hg, which according to the gas chromatogram is more than 98% pure, are obtained. The bulk of the material boils at 74° C./0.018 mm Hg.

Analysis $C_9H_{32}NO_3P$ (M=223.25). Calculated: C 48.42; H 9.93; N 6.27; P 13.87. Found: C 48.08; H 9.92; N 6.26; P 13.70.

EXAMPLE 10

Y-Aminopropyl-phosphonic acid diisooctyl ester

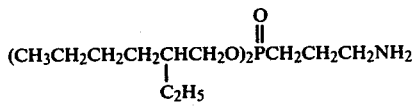

166.0 g of β-cyanoethyl-phosphonic acid diisooctyl ester in a mixture of 400 ml of toluene and 150 g of gaseous ammonia are hydrogenated in the presence of 13 g of Raney nickel in an autoclave for 7 hours at 90° C. and an initial pressure of 100 atmospheres gauge. The reaction is already complete after 4 hours (constant final pressure). After working up as in Example 1, 166.2 g of crude amine containing (as shown by titration with acid) 2.62 amine equivalents per kg (theoretical 2.76 equivalents per kg) are obtained. For the analysis, 12.55 g are distilled in a high vacuum, giving 10.72 g of amine of boiling point 137° C./0.007 mm Hg.

Analysis $C_{19}H_{42}NO_3P$ (M=363.52). Calculated: N 3.85; P 8.52. Found: N 3.71; P 8.26.

EXAMPLE 11

Y-Amino-α-phenyl)-propyl-phosphonic acid diisopropyl ester

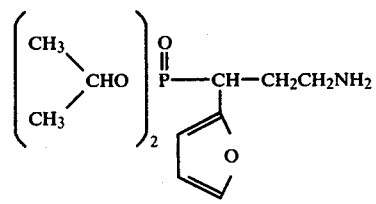

101.6 g of (β-cyano-α-phenyl)-ethyl-phosphonic acid diisopropyl ester in a mixture of 400 ml of isopropanol and 100 g of gaseous ammonia are hydrogenated for 4 hours in the presence of 10 g of Raney nickel in an autoclave at 80° C. and a pressure of 100 atmospheres gauge. After working up as in Example 1, 101.0 g (98% of theory) of crude amine, which (as shown by titration with acid) contains 3.30 amine equivalents per kg (theoretical 3.36 equivalents per kg) are obtained. For the analysis, 12.0 g were distilled in a high vacuum, giving 10.69 g of amine of boiling point 104°–105° C./0.008 mm Hg.

Analysis $C_{15}H_{26}NO_3P$ (M=299.35) Calculated: C 60.18; H 8.75; N 4.68; P 10.35. Found: C 60.17; H 8.72; N 4.68; P 10.42.

The aromatic protons of the phenyl radical can be detected by means of the NMR spectrum; hence, no change occurred in this part of the molecule during hydrogenation.

A further sample of 12.6 g of crude amine was distilled at a pressure of 1.0 mm Hg and gave 11.19 g of pure distillate of boiling point 170° C./1.0 mm Hg. No impurities were detectable by gas chromatography in this distillate.

EXAMPLE 12

(Y-Amino-α-furyl)-propyl-phosphonic acid diisopropyl ester 41.9 g of (β-cyano-β-furyl-ethyl-phosphonic acid diisopropyl ester in a mixture of 180 ml of isopropanol and 50 g of gaseous ammonia were hydrogenated for 2.5 hours in the presence of 5 g of Raney nickel in an autoclave at 100° C. and a pressure of 70 atmospheres gauge. Working up as in Example 1 gives 41.7 g of crude amine.

For the analysis, 8.2 g were distilled in a high vacuum, during which 5.8 g of pure amine of boiling point 78° C./0.009 mm Hg passed over. Only traces of by-products are detectable in the gas chromatogram.

What we claim is:

1. Process for the manufacture of aminoalkylphosphonic acid esters of the general formula I

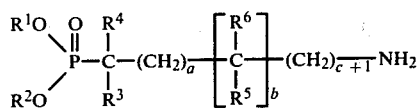

(I)

in which
R[1] and R[2] are identical or different and denote an unbranched or branched alkyl radical with 2 to 10 carbon atoms, a cycloaliphatic radical or, together, an alkyl-substituted or unsubstituted propylene radical, a, b and c are identical or different and a and c denote a number from 0 to 5 and b denotes 0 or 1, R[3] represents hydrogen, an alkyl radical with 1 to 10 carbon atoms, phenyl or furyl and R[4], R[5] and R[6] are identical or different and denote hydrogen or the methyl group, characterised in that a cyanoalkylphosphonic acid ester of the general formula II

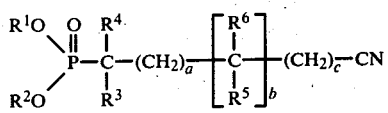

(II)

is hydrogenated catalytically using a nickel catalyst at temperatures of about 20° to 150° C. and the resulting product is freed in a known manner from the catalyst and solvents and is optionally distilled, preferably in a high vacuum.

2. Process according to claim 1, characterised in that compounds according to the formula II, in which R[1] and R[2] each denote a branched alkyl radical with the branching in the α- or β-position to the oxygen atom and with a total of 3 to 8 C atoms, are employed.

3. Process according to claim 1, characterised in that compounds according to the formula II, in which R[1] and R[2] are identical, are employed.

4. Process according to claim 1, characterised in that compounds according to the formula II, in which R[3] denotes hydrogen, methyl, phenyl or furyl, are employed.

5. Process according to claim 1, characterised in that cyanoalkyl-phosphonic acid esters according to the formula II, which contain an unbranched or branched alkylene radical with a total of 1 to 3 carbon atoms between the P atom and the nitrile group, are employed.

6. Process according to claim 1, characterised in that the hydrogenation is carried out at temperatures of 60° to 120° C.

7. Process according to claim 1, characterised in that the hydrogenation is carried out in the presence of ammonia.

8. Process according to claim 1, characterised in that the product obtained by hydrogenation is distilled at a temperature such that boiling points of 150° to 170° C. are not exceeded.

* * * * *